Figure 1:
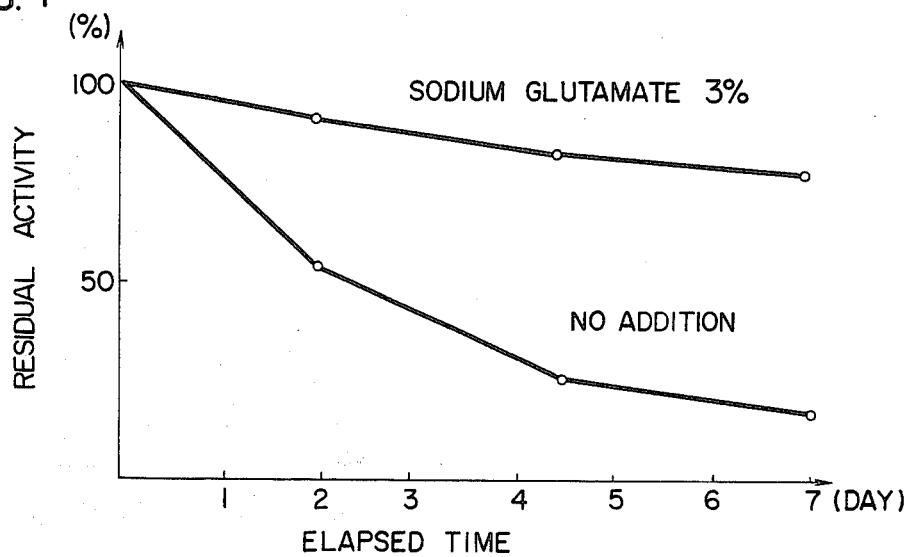

United States Patent [19]

Miyashita et al.

[11] Patent Number: 4,543,326

[45] Date of Patent: Sep. 24, 1985

[54] STABILIZATION OF OXIDASE

[75] Inventors: Yoshinobu Miyashita; Shinji Satomura, both of Osaka, Japan

[73] Assignee: Wako Pure Chemical Industries, Ltd., Osaka, Japan

[21] Appl. No.: 441,156

[22] Filed: Nov. 12, 1982

[30] Foreign Application Priority Data

Nov. 12, 1981 [JP] Japan .................................. 56-181443

[51] Int. Cl.$^4$ .......................... C12Q 1/48; C12Q 1/54; C12Q 1/44; C12Q 1/46

[52] U.S. Cl. ........................................ 435/15; 435/14; 435/19; 435/20; 435/25; 435/28; 435/188; 435/810

[58] Field of Search ................. 435/14, 188, 190, 20, 435/28, 25, 15, 18, 19, 810, 805, 11; 424/94

[56] References Cited

U.S. PATENT DOCUMENTS

| | | | |
|---|---|---|---|
| 3,096,251 | 7/1963 | Babson | 435/188 |
| 3,539,450 | 11/1970 | Deutsch | 435/188 |
| 3,964,974 | 6/1976 | Banauch et al. | 435/4 |
| 4,135,980 | 1/1979 | Ikuta et al. | 435/19 |
| 4,241,178 | 12/1980 | Esders et al. | 435/19 |
| 4,245,050 | 1/1981 | Nakanishi et al. | 435/25 |
| 4,275,161 | 6/1981 | Misaki et al. | 435/190 |
| 4,279,993 | 7/1981 | Magers et al. | 435/14 |
| 4,288,541 | 9/1981 | Magers et al. | 435/28 |

FOREIGN PATENT DOCUMENTS 55-34001  3/1980  Japan .................................. 435/188

OTHER PUBLICATIONS

Barman, *Enzyme Handbook*, vol. I, Springer-Verlag, New York, 112-113 (1969).
Chemi Abstract 93, 68683a (1980).
Chem. Abstract 97, 19847f (1982).

*Primary Examiner*—Esther M. Kepplinger
*Attorney, Agent, or Firm*—Armstrong, Nikaido, Marmelstein & Kubovcik

[57] ABSTRACT

An oxidase selected from the group consisting of glycerol-3-phosphate oxidase, choline oxidase and glucose oxidase can be stabilized by adding thereto an acidic amino acid or a salt thereof. The resulting stabilized composition can be used for quantitatively determining the content of glycerol-3-phosphate, choline, triglyceride, glucose, etc., in a biological fluid.

28 Claims, 7 Drawing Figures

STABILIZATION OF OXIDASE

This invention relates to a process for stabilizing an oxidase and a composition containing the stabilized oxidase for use in clinical chemical examinations.

Recently, clinical chemical examinations have been developed remarkably as examination techniques for diagnosis of diseases and watching of the course of treatments. Particularly, the progress and spread of automatic chemical analysis equipments makes the examinations not only rapid and accurate but also more important in hospital examinations. The automatic chemical analysis equipment require new types of measuring reagents. That is, the reagents should complete the reaction in a short time at a mild temperature such as about 37° C. in order to be appropriate for such equipments. Thus, enzymatic measuring methods using enzymes have been developed. At present, almost all blood components can be determined quantitatively by enzymatic methods.

In such enzymatic methods, it becomes important to stabilize a reagent solution containing an enzyme for a long period of time. For example, measurement of neutral fat (triglyceride) is an important test, in the detection of abnormal lipids metabolism, diagnosis of diseases such as diabetes mellitus, and assessment of the course of treatment. For measuring triglyceride, glycerol-3-phosphate oxidase is used. But glycerol-3-phosphate oxidase is not good in stability, particularly in an aqueous solution.

It is also known that oxidases are generally unstable. Stabilization of oxidases other than glycerol-3-phosphate oxidase is also desirable. Examples of such oxidases are choline oxidase, glucose oxidase, etc.

The main constituent of enzymes are proteins. Enzymes show special enzymatic actions depending on the space structures of these proteins. However, the space structures are affected by various factors and thus enzymes lose their activities. Therefore, it is necessary to stabilize the enzymes.

There have been proposed many processes for stabilizing enzymes. One process consists of adding a substrate or a coenzyme to an enzyme to be stabilized. In proteins of enzymes, there are one or more local portions having strain which are unstable from the viewpoint of energy. Such portions often become the active portions of enzymes. When a substrate or a coenzyme is bonded to such portions, such portions are stabilized from the viewpoint of energy, which results in stabilizing the enzymes. Another process is to add a SH protecting reagent to enzymes. When an enzyme has an active portion having a SH group, it is effective to add a SH protecting reagent such as mercaptoethanol, dithiothreitol or the like to such an enzyme. Further, non-specific stabilizers are sometimes used. For example, inert proteins such as albumin, glycerol, lactose, etc. are sometimes effective.

But, in the case of oxidases such as glycerol-3-phosphate oxidase, cholin oxidase, glucose oxidase, etc., such stabilizing methods or stabilizers as mentioned above are not effective at all.

The objects of this invention are to provide a process for stabilizing oxidases, and a composition containing such a stabilized oxidase for use in clinical chemical examinations.

This invention provides a process for stabilizing an oxidase selected from the group consisting of glycerol-3-phosphate oxidase, choline oxidase and glucose oxidase which comprises adding an acidic amino acid or a salt thereof to said oxidase.

This invention also provides a composition for use in clinical chemical examinations comprising an oxidase selected from the group consisting of glycerol-3-phosphate oxidase, choline oxidase and glucose oxidase, and an acidic amino acid or a salt thereof.

Figure 3:
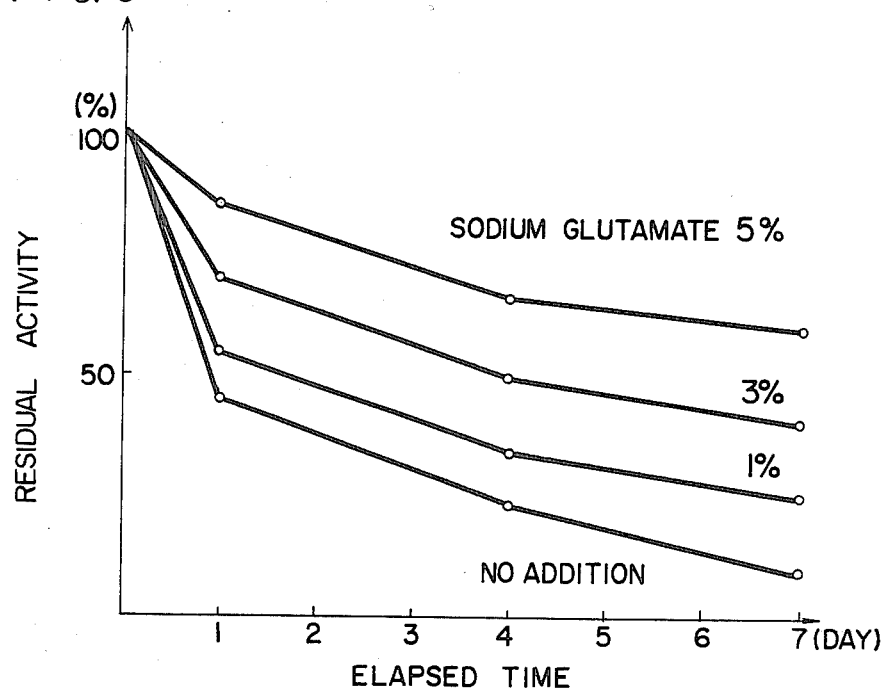
Figure 4:
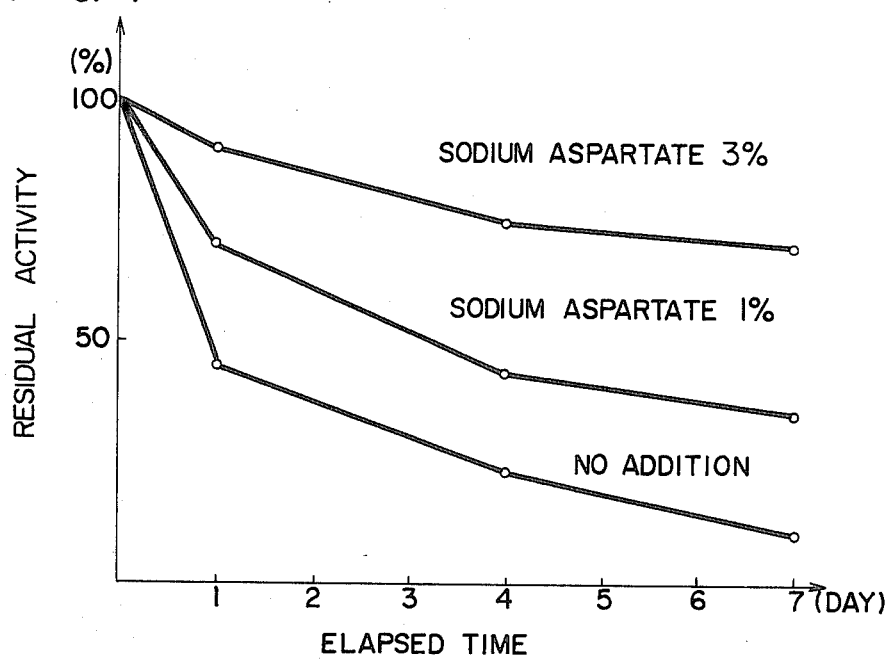
Figure 5:
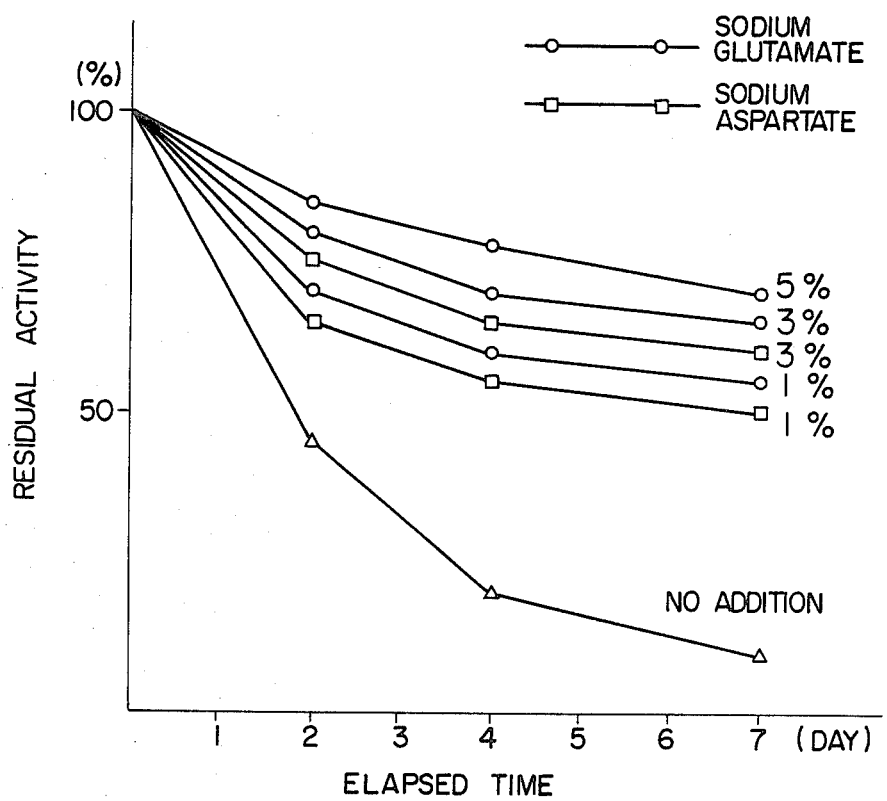
Figure 6:
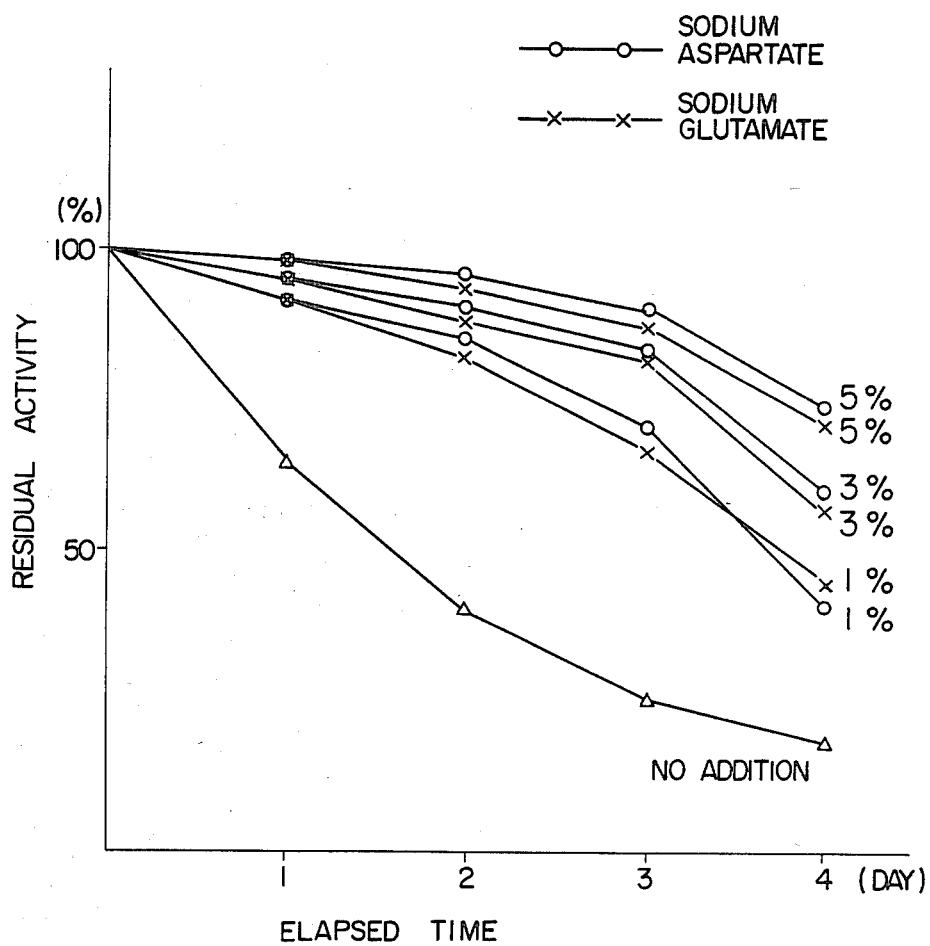
Figure 7:
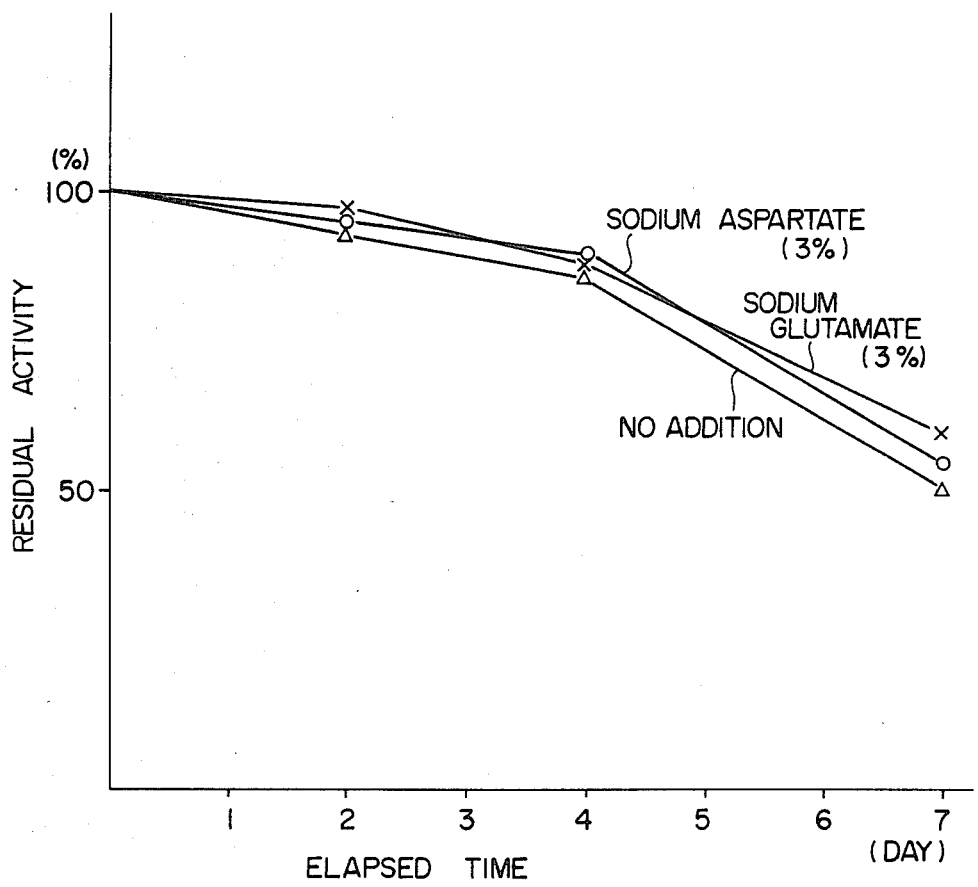

In the attached drawings,

FIGS. 1 to 4 show the relationships between residual activity of glycerol-3-phosphate oxidase and elapsed time with or without addition of the salt of acidic amino acid, FIG. 5 shows a relationship between residual activity of choline oxidase and elapsed time with or without addition of a salt of acidic amino acid, FIG. 6 shows the relationship between residual activity of glucose oxidase and elapsed time with or without addition of a salt of acidic amino acid, and FIG. 7 shows the relationship between residual activity of cholesterol oxidase and elapsed time with or without addition of a salt of acidic amino acid (comparison).

It is a very important and surprising thing that the addition of an acidic amino acid (aminodicarboxylic acid) or a salt thereof to an oxidase selected from the group consisting of glycerol-3-phosphate oxidase, choline oxidase and glucose oxidase makes the oxidase stabilized without giving undesirable influences on the measurement in clinical chemical examinations to be conducted afterward.

The stabilizing agent usable in this invention is an acidic amino acid or a salt thereof, preferably a buffer solution-soluble salt thereof. Such a stabilizing agent is preferably represented by the formula:

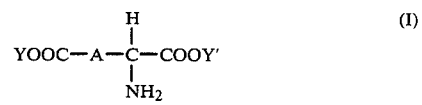

$$YOOC-A-\underset{NH_2}{\overset{H}{\underset{|}{C}}}-COOY' \qquad (I)$$

wherein A is a lower alkylene group preferably having 1 to 5 carbon atoms; and Y and Y' are independently hydrogen, a $NH_4$ group or an alkali metal. Preferable examples of the acidic amino acid of the formula (I) are glutamic acid, aspartic acid, mono- or diammonium salt of glutamic acid or aspartic acid, mono or dialkali metal salts of glutamic or aspartic acid such as sodium glutamate, sodium aspartate, potassium glutamate, potassium aspartate, etc. The use of alkali metal salt of glutamic or aspartic acid is preferable considering solubility. It is possible to use other acidic amino acids such as α-aminoadipic acid, and the like.

The acidic amino acid or a salt thereof is added in an amount of 1 to 5% by weight to the aqueous solution containing an oxidase to be stabilized. The oxidase content in the aqueous solution changes depending on the kinds of oxidases to be stabilized but usually 1 to 20 units/ml (U/ml) for glycerol-3-phosphate oxidase and choline oxidase and 1 to 100 U/ml for glucose oxidase. If the amount is too much, the stability of coloring in the clinical chemical examination is damaged. Usually, about 3% by weight is more preferable.

Oxidases to be stabilized by this invention are glycerol-3-phosphate oxidase, choline oxidase and glucose oxidase. Although these oxidases belong to flavin enzymes, the stabilizing process of this invention is only applicable to limited members of flavin enzymes. For example, the process of this invention is not effective for cholesterol oxidase which belongs to flavin enzymes.

Glycerol-3-phosphate oxidase is an oxidase which can be obtained via culture and extraction from strains of Aerococcus or Streptococcus, but it is unstable particularly in the form an aqueous solution.

Glycerol-3-phosphate oxidase is used, for example, for measuring triglyceride. Triglyceride (neutral fat) was measured by using enzymes as follows:

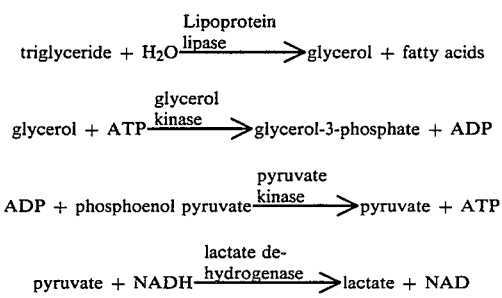

$$triglyceride + H_2O \xrightarrow{\text{Lipoprotein lipase}} glycerol + fatty\ acids$$

$$glycerol + ATP \xrightarrow{\text{glycerol kinase}} glycerol\text{-}3\text{-}phosphate + ADP$$

$$ADP + phosphoenol\ pyruvate \xrightarrow{\text{pyruvate kinase}} pyruvate + ATP$$

$$pyruvate + NADH \xrightarrow{\text{lactate dehydrogenase}} lactate + NAD$$

That is, by measuring a decrease in absorbance at 340 nm at which NADH shows a specific absorption, the content of triglyceride in a sample can be obtained. According to this method, since the absorbance at 340 nm belongs to the ultraviolet region, it is necessary to use an ultraviolet spectrophotometer and further when serum is used as a sample, specimen blank gives great influence on measuring.

But, recently, a colorimetric method using wavelengths in the visible light region is developed in contrast to the above-mentioned method. Such a method uses glycerol-3-phosphate oxidase and can be represented by the following equations:

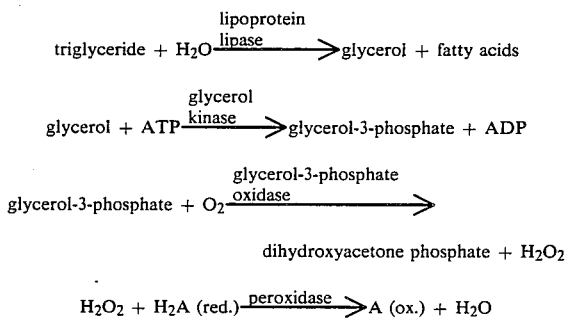

$$triglyceride + H_2O \xrightarrow{\text{lipoprotein lipase}} glycerol + fatty\ acids$$

$$glycerol + ATP \xrightarrow{\text{glycerol kinase}} glycerol\text{-}3\text{-}phosphate + ADP$$

$$glycerol\text{-}3\text{-}phosphate + O_2 \xrightarrow{\text{glycerol-3-phosphate oxidase}} dihydroxyacetone\ phosphate + H_2O_2$$

$$H_2O_2 + H_2A\ (red.) \xrightarrow{\text{peroxidase}} A\ (ox.) + H_2O$$

In the above-mentioned reaction equations, when an indicator which produces a color in a visible light region is used, it becomes possible to employ a colorimetric method in the visible light region while overcoming disadvantages of the old process mentioned above. Thus, to stabilize an aqueous solution of glycerol-3-phosphate oxidase becomes very important.

Choline oxidase is an oxidase which can be obtained from strains of Arthrobacter or Alcaligenes.

Choline oxidase accelerates the following reaction:

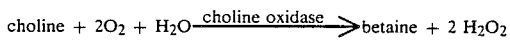

$$choline + 2O_2 + H_2O \xrightarrow{\text{choline oxidase}} betaine + 2\ H_2O_2$$

Therefore, in a system wherein choline is present or choline is produced, it becomes possible to employ a colorimetric method in the visible light region wherein $H_2O_2$ produced is measured. Further, as applications of choline oxidase to quantitative methods of living samples, it is possible to measure the activity of choline esterase and to measure quantitatively the amount of phospholipids wherein phospholipase D is combined and liberated choline is measured.

Glucose oxidase is an oxidase which can be obtained from strains of Aspergillus and accelerates the following reaction:

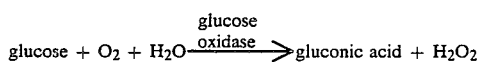

$$glucose + O_2 + H_2O \xrightarrow{\text{glucose oxidase}} gluconic\ acid + H_2O_2$$

Glucose oxidase has wide applications for measuring living samples, for example, quantitative determination of glucose in a body fluid, measuring of activity of amylase, etc. In measuring the activity of amylase using starch as a substrate, glucose obtained by decomposition of starch via glucoamylase is measured quantitatively.

In the following description, explanations will be given for a stabilized reagent composition containing glycerol-3-phosphate oxidase for measuring glycerol-3-phosphate and the like. A reagent solution containing glycerol-3-phosphate oxidase, peroxidase and an indicator, said reagent solution per se being known for measuring glycerol-3-phosphate quantitatively, can be stabilized by adding an acidic amino acid or a salt thereof such as alkali metal salt of aminodicarboxylic acid thereto. Thus, a stabilized reagent composition for use in clinical applications can be obtained, said composition containing glycerol-3-phosphate oxidase, an alkali metal salt of aminodicarboxylic acid as a stabilizer and a buffer solution, and if necessary an indicator for colorimetric determination and one or more conventional additives.

In the same manner as mentioned above, stabilized reagent compositions comprising choline oxidase or glucose oxidase, a stabilizer of the formula (I), and a buffer solution, and if necessary one or more conventional additives such as an indicator for colorimetric determination, and the like can be obtained.

In the case of measuring the content of triglyceride in a living sample such as serum, etc., there can be used a reagent solution for measurement prepared by dissolving lipoprotein lipase, glycerol kinase, ATP, glycerol-3-phosphate oxidase, peroxidase and an indicator in a suitable buffer solution such as tris buffer solution.

In the reaction using such a reagent composition, hydrogen peroxide ($H_2O_2$) is produced from glycerol-3-phosphate by the action of glycerol-3-phosphate oxidase. When an oxidizable color producing indicator is present in such a case, said indicator produces the color by $H_2O_2$ in the presence of peroxidase.

As the oxidizable color producing indicator, there can be used o- or p-phenylenediamine, dianisidine, and the like indicators alone, or a combination indicator such as 4-aminoantipyrine and phenol, a halophenol or an aniline derivative, etc.

As the buffer solution, there can be used any ones which can maintain the desired pH. Examples of such buffer solutions are a tris buffer solution, Good buffer solution, phosphate buffer solution, and the like. The pH preferable for the reaction is near neutral value, and pH 7.5 is more preferable.

Further, as is clear from the reaction equations mentioned above, any substances such as triglyceride, glycerol, ATP, and glycerol-3-phosphate can be measured.

But the most important reaction step among these reaction equations is the reaction using glycerol-3-phosphate oxidase.

Glycerol-3-phosphate oxidase obtained from Aerococcus viridans or Streptococcus faecalis by a conventional process is very unstable in an aqueous solution and can only be used for a few hours after dissolving.

But according to the stabilizing process of this invention, an aqueous solution of glycerol-3-phosphate oxidase can be stored at 5° C. for one week stably by adding an aminodicarboxylic acid (acidic amino acid) or a salt thereof and can be used for measurement during such a period. (See FIGS. 1 to 4.)

In the same manner as mentioned above, an aqueous solution of choline oxidase can be stabilized and can be used for measurement after being stored at 20° C. for one week, and an aqueous solution of glucose oxidase can be used for measurement after being stored at 40° C. for 3 days. (See FIGS. 5 and 6.)

This invention is illustrated by way of the following Examples.

EXAMPLE 1

(1) Determination of Glycerol-3-phosphate

Reagent Solution

A reagent solution for measuring glycerol-3-phosphate was prepared by dissolving the following ingredients in 0.05M tris buffer solution (pH 7.5):

| Glycerol-3-phosphate oxidase | 5 U/ml |
| --- | --- |
| Peroxidase | 2.5 U/ml |
| p-Chlorophenol | 0.07% by weight |
| 4-Aminoantipyrine | 0.15 mg/ml |
| Sodium glutamate | 3.0% by weight |

Measuring Operations

A sample (e.g. a biological fluid such as serum) in an amount of 0.02 ml was added to 3.0 ml of the reagent solution for measurement obtained by the above formulation. After mixing well, color was produced by warming at 37° C. for 10 minutes. On the other hand, using 0.02 ml of distilled water, a reagent blank was prepared in the same manner as mentioned above.

Absorbances at 505 nm were measured using the reagent blank as control. Absorbances of standard solutions prepared by dissolving certain amounts of glycerol-3-phosphate in various concentrations were also measured in the same manner as mentioned above and the content of glycerol-3-phosphate in the sample was obtained by proportion calculations based on the absorbances obtained.

(2) Stabilization of Aqueous Solution of Glycerol-3-phosphate Oxidase

A 0.05M tris buffer solution (pH 7.5) dissolving 0.07% by weight of p-chlorophenol, 5 U/ml of glycerol-3-phosphate oxidase and 3.0% by weight of sodium glutamate was maintained at 5° C. and residual activity of glycerol-3-phosphate oxidase was measured with the lapse of time. For comparison, the same composition as mentioned above except for not containing sodium glutamate was also prepared and measured in the same manner as mentioned above.

The results are as shown in FIG. 1.

Figure 2:
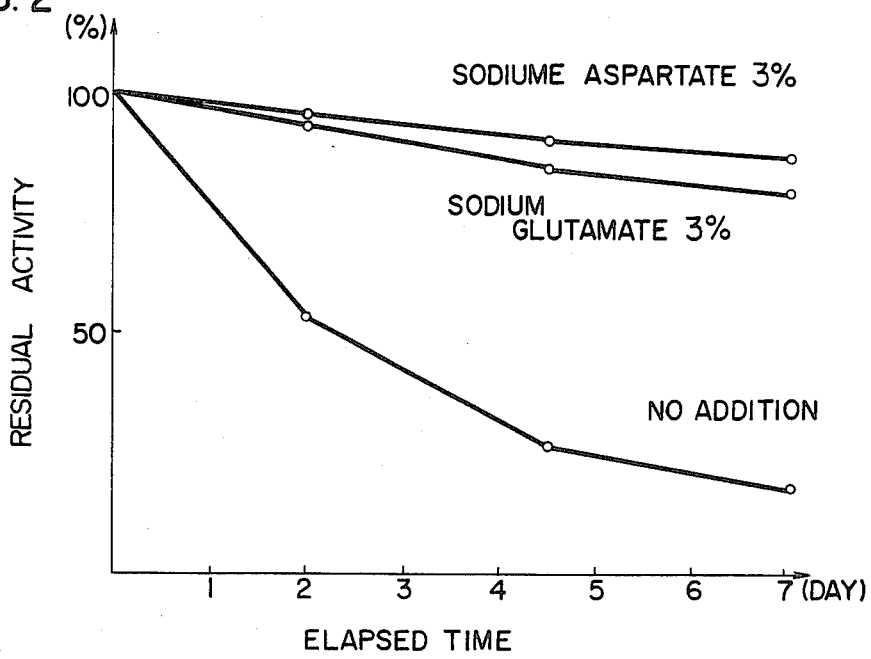

When 3.0% by weight of sodium aspartate was used in place of sodium glutamate, the results are as shown in FIG. 2, which also shows the results of FIG. 1.

When sodium glutamate was dissolved in a 0.05M tris buffer solution (pH 7.5) in various concentrations (5%, 3%, 1%, and 0% by weight) together with 5 U/ml of glycerol-3-phosphate oxidase and kept at 20° C., the residual activity of glycerol-3-phosphate oxidase with the lapse of time was as shown in FIG. 3.

When sodium aspartate was dissolved in a 0.05M tris buffer solution (pH 7.5) in various concentrations (3%, 1% and 0% by weight) together with 5 U/ml of glycerol-3-phosphate oxidase and kept at 20° C., the residual activity of glycerol-3-phosphate oxidase with the lapse of time was as shown in FIG. 4.

EXAMPLE 2

Determination of Triglyceride in a Living Sample

Reagent Solution

A reagent solution for measuring triglyceride was prepared by dissolving the following ingredients in 0.05M tris buffer solution (pH 7.5):

| Lipoprotein lipase | 40 U/ml |
| --- | --- |
| Glycerol kinase | 2.5 U/ml |
| Glycerol-3-phosphate oxidase | 5 U/ml |
| Peroxidase | 2.5 U/ml |
| Magnesium acetate | 5 mmoles/l |
| p-Chlorophenol | 0.07% by weight |
| 4-Aminoantipyrine | 0.15 mg/ml |
| ATP | 1 mg/ml |
| Sodium glutamate | 3% by weight |

Measuring Operations

A living sample or biological fluid (e.g. serum) in an amount of 0.02 ml was added to 3.0 ml of the reagent solution for measuring triglyceride and mixed well. Color was produced by warming at 37° C. for 10 minutes. On the other hand, using 0.02 ml of distilled water, a reagent blank was prepared in the same manner as mentioned above.

Absorbances at 505 nm were measured using the reagent blank as control. Absorbances of standard solutions prepared by dissolving certain amounts of glycerol in various concentrations were also measured. The glycerol content was obtained by proportion calculations, after which the triglyceride content was calculated by converting to the triglyceride amount.

EXAMPLE 3

(1) Determination of Choline

Reagent Solution

A reagent solution for measuring choline was prepared by dissolving the following ingredients in a 0.05M phosphate buffer solution (pH 7.6):

| Choline oxidase | 2.5 U/ml |
| --- | --- |
| Peroxidase | 1.0 U/ml |
| 4-Aminoantipyrine | 0.015% by weight |
| Phenol | 0.1% by weight |
| Sodium glutamate | 3.0% by weight |

Measuring Operations

A sample (e.g. a biological fluid such as serum) in an amount of 0.02 ml was added to 3.0 ml of the reagent solution for measuring choline and mixed well. Color was produced by warming at 37° C. for 10 minutes. On the other hand, using 0.02 ml of distilled water, a reagent blank was prepared in the same manner as mentioned above.

Absorbances at 505 nm were measured using the reagent blank as control. Absorbances of standard solutions prepared by dissolving certain amounts of choline chloride in various concentrations were also measured. The choline content in the sample was obtained by proportion calculations based on the absorbances obtained.

(2) Stabilization of Aqueous Solution of Choline Oxidase

A 0.05M phosphate buffer solution (pH 7.6) dissolving 2.5 U/ml of choline oxidase and 0.1% by weight of phenol together with sodium glutamate (5%, 3%, 1% and 0% by weight) or sodium aspartate (3%, 1% and 0% by weight) was maintained at 20° C. The residual activity of choline oxidase was measured with the lapse of time and shown in FIG. 5.

EXAMPLE 4

Measurement of Activity of Choline Esterase in Living Sample

Reagent Solution (A) Substrate enzyme solution

A substrate enzyme solution was prepared by dissolving the following ingredients in a 0.02M phosphate buffer solution (pH 7.6):

| Choline oxidase | 2.5 U/ml |
| --- | --- |
| Peroxidase | 1.0 U/ml |
| 4-Aminoantipyrine | 0.015% by weight |
| Choline benzoyl chloride | 0.015% by weight |
| Phenol | 0.2% by weight |
| Sodium glutamate | 3.0% by weight |

(B) Reaction stopper solution

A reaction stopper solution was prepared by dissolving 100 mg of neostigmine methylsulfate in 100 ml of distilled water.

Measuring Operations

In a test tube, 2.0 ml of the substrate enzyme solution was placed and warmed at 37° C. for 3 minutes in a constant temperature water bath. Subsequently, 0.02 ml of a sample (e.g. a biological fluid such as serum) was added to the test tube and mixed well. After warming at 37° C. for just 5 minutes, 2.0 ml of the reaction stopper solution was added thereto. On the other hand, using 0.02 ml of distilled water, a reagent blank was prepared in the same manner as mentioned above.

Absorbances at 505 nm were measured using the reagent blank as control. Absorbances of serum having known activity values were measured in same manner as mentioned above and activity value of choline esterase in the sample was obtained by proportion calculations based on the absorbances obtained.

EXAMPLE 5

(1) Determination of Glucose

Reagent Solution

A reagent solution for measuring glucose was prepared by dissolving the following ingredients in a 0.2M phosphate buffer (pH 7.4):

| Glucose oxidase | 30 U/ml |
| --- | --- |
| Mutarotase | 0.1 U/ml |
| Peroxidase | 1.0 U/ml |
| 4-Aminoantipyrine | 0.1% by weight |
| Phenol | 0.1% by weight |
| Sodium aspartate | 5.0% by weight |

Measuring Operations

A sample (e.g. a biological fluid such as serum) in an amount of 0.02 ml was added to 3.0 ml of the reagent solution for measuring glucose and mixed well. Color was produced by warming at 37° C. for 10 minutes. On the other hand, using 0.02 ml of distilled water, a reagent blank was prepared in the same manner as mentioned above.

Absorbances at 505 nm were measured using the reagent blank as control. Absorbances of standard solutions prepared by dissolving certain amounts of glucose in various concentration were also measured. The glucose content in the sample was obtained by proportion calculations of the absorbances obtained.

(2) Stabilization of Aqueous Solution of Glucose Oxide

A 0.2M phosphate buffer solution (pH 7.4) dissolving 30 U/ml of glucose oxidase and 0.1% by weight of phenol together with sodium glutamate (5%, 3%, 1% and 0% by weight) or sodium aspartate (5%, 3%, 1% and 0% by weight) was maintained at 40° C. The residual activity of glucose oxidase was measured with the lapse of time and shown in FIG. 6.

COMPARATIVE EXAMPLE 1

(1) Determination of Cholesterol

Reagent Solution

A reagent solution for measuring cholesterol was prepared by dissolving the following ingredients in a 0.1M phosphate buffer solution (pH 7.0):

| Cholesterol oxidase | 0.2 U/ml |
| --- | --- |
| Peroxidase | 1.0 U/ml |
| 4-Aminoantipyrine | 0.015% by weight |
| Phenol | 0.1% by weight |

Measuring Operations

A sample (e.g. a biological fluid such as serum) in an amount of 0.02 ml was added to 3.0 ml of the reagent solution for measuring cholesterol and mixed well. Color was produced by warming at 37° C. for 10 minutes. On the other hand, using 0.02 ml of distilled water, a reagent blank was prepared in the same manner as mentioned above.

Absorbances at 505 nm were measured using the reagent blank as control. Absorbances of standard solutions prepared by dissolving certain amounts of cholesterol in isopropyl alcohol in various concentrations were also measured. The cholesterol content in the sample was obtained by proportion calculations of the absorbances obtained. The same results were also obtained when sodium aspartate or sodium glutamate (3% by weight) was added to the reagent solution.

(2) Stabilization of Aqueous Solution of Cholesterol Oxidase

A 0.1M phosphate buffer solution (pH 7.0) dissolving 0.2 U/ml of cholesterol oxidase and 0.1% by weight of phenol together with sodium glutamate (3% by weight) or sodium aspartate (3% by weight) or without sodium glutamate or sodium aspartate was maintained at 20° C. The residual activity of cholesterol oxidase was measured with the lapse of time and shown in FIG. 7.

As shown in FIG. 7, there is shown no stabilizing effect of sodium aspartate or sodium glutamate in the case of aqueous solution of cholesterol oxidase.

What is claimed is:

1. A process for stabilizing an oxidase which comprises adding an acidic amino acid or a salt thereof in an amount of 1 to 5% by weight to an aqueous solution of an oxidase selected from the group consisting of glycerol-3-phosphate oxidase, and choline oxidase.

2. A process according to claim 1, wherein the oxidase is glycerol-3-phosphate oxidase.

3. A process according to claim 1, wherein the oxidase is choline oxidase.

4. A process according to claim 1, wherein the acidic amino acid or a salt thereof is a buffer solution-soluble salt of acidic amino acid.

5. A process according to claim 1, wherein the acidic amino acid or a salt thereof is represented by the formula:

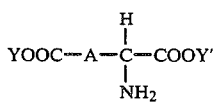

wherein A is a lower alkylene group having 1 to 5 carbon atoms; and Y and Y' are independently hydrogen, a NH$_4$ group or an alkali metal.

6. A process according to claim 1, wherein the acidic amino acid or a salt thereof is sodium glutamate.

7. A process according to claim 1, wherein the acidic amino acid or a salt thereof is sodium aspartate.

8. A process for quantitatively determining the glycerol-3-phosphate content in a biological fluid which comprises adding to the biological fluid an aqueous solution containing
glycerol-3-phosphate oxidase in an amount of 1 to 20 units/ml,
a buffer solution in an amount sufficient to maintain the pH near neutral value,
an acidic amino acid or a salt thereof in an amount of 1 to 5% by weight based on the weight of the aqueous solution containing the oxidase,
peroxidase, 4-aminoantipyrine, and an oxidizable color producing indicator in amounts sufficient to produce a color,
and measuring the color produced colorimetrically.

9. A process according to claim 8, wherein the acidic amino acid or a salt thereof is an alkali metal salt of acidic amino acid.

10. A process according to claim 9, wherein the alkali metal salt of acidic amino acid is sodium aspartate or sodium glutamate.

11. A process for quantitatively determining the triglyceride content in a biological fluid which comprises adding to the biological fluid an aqueous solution containing
glycerol-3-phosphate oxidase in an amount of 1 to 20 units/ml,
a buffer solution in an amount sufficient to maintain the pH near neutral value,
an acidic amino acid or a salt thereof in an amount of 1 to 5% by weight of the aqueous solution,
lipase, glycerol kinase, peroxidase, 4-aminoantipyrine and an oxidizable color producing indicator in amounts sufficient to produce a color,
and measuring the color produced colorimetrically.

12. A process according to claim 11, wherein the acidic amino acid or a salt thereof is an alkali metal salt of acidic amino acid.

13. A process according to claim 12, wherein the alkali metal salt of acidic amino acid is sodium aspartate or sodium glutamate.

14. A process for quantitatively determining the choline content in a biological fluid which comprises adding to the biological fluid an aqueous solution containing
choline oxidase in an amount of 1 to 20 units/ml,
a buffer solution in an amount sufficient to maintain the pH near neutral value,
an acidic amino acid or a salt thereof in an amount of 1 to 5% by weight, based upon the weight of the aqueous solution,
peroxidase, 4-aminoantipyrine and an oxidizable color producing indicator in sufficient amounts to produce a color, and
measuring the color produced colormetrically.

15. A process according to claim 14, wherein the acidic amino acid or a salt thereof is an alkali metal salt of acidic amino acid.

16. A process according to claim 15, wherein the alkali metal salt of acidic amino acid is sodium aspartate or sodium glutamate.

17. A process for measuring the activity of choline esterase in a biological fluid which comprises adding to the biological fluid an aqueous solution containing
choline oxidase in an amount of 1 to 20 units/ml,
a buffer solution in an amount of 1 to 5% by weight based on the weight of the solution,
peroxidase, choline benzoyl chloride, 4-aminoantipyrine and an oxidizable color producing indicator in amounts sufficient to produce a color,
adding to the resulting mixture a reaction stopper solution, and
measuring the color produced colorimetrically.

18. A process according to claim 17, wherein the acidic amino acid or a salt thereof is an alkali metal salt of acidic amino acid.

19. A process according to claim 18, wherein the alkali metal salt of acidic amino acid is sodium aspartate or sodium glutamate.

20. A process according to any of claims 1, 8, 11, 14, or 17 in which the acidic amino acid is selected from the group consisting of glutamic acid, aspartic acid, alpha-aminoadipic acid and salts of these acidic amino acids.

21. A stabilized composition comprising
an oxidase selected from the group consisting of glycerol-3-phosphate oxidase, and choline oxidase,
an acidic amino acid or a salt thereof in an amount equal to 1 to 5% by weight of the composition, and a buffer solution in an amount sufficient to maintain the pH near neutral value.

22. A composition according to claim 21, wherein the oxidase is glycerol-3-phosphate oxidase.

23. A composition according to claim 21, wherein the oxidase is choline oxidase.

24. A stabilized composition according to claim 21, wherein the acidic amino acid or a salt thereof is represented by the formula:

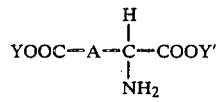

wherein A is a lower alkylene group having 1 to 5 carbon atoms; and Y and Y' are independently hydrogen, a $NH_4$ group or an alkali metal.

25. A composition according to claim 21, which further comprises a color producing reagent.

26. A composition according to claim 21, wherein the acidic amino acid or a salt thereof is sodium glutamate.

27. A composition according to claim 21, wherein the acidic amino acid or a salt thereof is sodium aspartate.

28. A composition according to claim 21 in which the acidic amino acid is selected from the group consisting of glutamic acid, aspartic acid, alpha-aminoadipic acid and salts of these acidic amino acids.

* * * * *